United States Patent
Goodwin et al.

(10) Patent No.: US 7,153,021 B2
(45) Date of Patent: Dec. 26, 2006

(54) CONTAINER SYSTEMS FOR MIXING FLUIDS WITH A MAGNETIC STIR BAR

(75) Inventors: Michael Goodwin, Logan, UT (US); Gregory P. Elgan, Providence, UT (US); Jeremy K. Larsen, Providence, UT (US)

(73) Assignee: Hyclone Laboratories, Inc., Logan, UT (US)

( * ) Notice: Subject to any disclaimer, the term of this patent is extended or adjusted under 35 U.S.C. 154(b) by 119 days.

(21) Appl. No.: 10/797,159

(22) Filed: Mar. 10, 2004

(65) Prior Publication Data

US 2004/0190372 A1    Sep. 30, 2004

Related U.S. Application Data

(60) Provisional application No. 60/458,677, filed on Mar. 28, 2003.

(51) Int. Cl.
    *B01F 13/08*    (2006.01)
(52) U.S. Cl. ..................................... 366/273
(58) Field of Classification Search ........ 366/273–274, 366/348–349; 604/416, 903; 215/DIG. 3, 215/DIG. 8; 206/219–221, 818; 416/3; 383/127
    See application file for complete search history.

(56) References Cited

U.S. PATENT DOCUMENTS

| | | | |
|---|---|---|---|
| 3,647,397 A * | 3/1972 | Coleman | 366/167.1 |
| 4,040,605 A | 8/1977 | Towsend | |
| 4,162,855 A | 7/1979 | Bender | |
| 4,199,265 A | 4/1980 | Sanderson et al. | |
| 4,209,259 A | 6/1980 | Rains et al. | |
| 4,290,300 A | 9/1981 | Carver | |
| 4,498,785 A | 2/1985 | de Bruyne | |
| 4,711,582 A * | 12/1987 | Kennedy | 366/279 |
| 4,805,799 A * | 2/1989 | Robbins, III | 366/348 |
| 4,830,511 A | 5/1989 | Smazik | |
| 4,901,886 A | 2/1990 | Kirschner | |
| 4,925,055 A * | 5/1990 | Robbins et al. | 220/495.06 |
| 4,994,057 A * | 2/1991 | Carmen et al. | 604/416 |
| 5,061,079 A | 10/1991 | Shiobara | |
| 5,141,327 A * | 8/1992 | Shiobara | 366/274 |
| 5,193,977 A | 3/1993 | Dame | |
| 5,222,808 A | 6/1993 | Sugarman et al. | |
| 5,240,856 A | 8/1993 | Goffe et al. | |
| 5,261,742 A | 11/1993 | Lockhart | |

(Continued)

FOREIGN PATENT DOCUMENTS

WO    93/18805    *    9/1993

(Continued)

OTHER PUBLICATIONS

Russ Musch, *Product Brief Form for HyClone Bioprocess Containers*, May 31, 2001.

(Continued)

Primary Examiner—Charles E. Cooley
(74) Attorney, Agent, or Firm—Workman Nydegger (57) ABSTRACT

A container system includes a substantially rigid container having a floor and a side wall upstanding therefrom. The side wall and floor bound a chamber. A magnetic mixer is disposed below the floor of the container. A mixing bag assembly is disposed within the chamber of the container. The mixing bag assembly includes a collapsible body having a first end and an opposing second end. The collapsible body bounds a compartment. A mixing dish is disposed at the second end of the collapsible body so as to communicate with the compartment thereof. A magnetic stir bar is disposed on the mixing dish.

38 Claims, 8 Drawing Sheets

U.S. PATENT DOCUMENTS

| | | | |
|---|---|---|---|
| 5,434,079 A | 7/1995 | Mozayeni | |
| 5,470,151 A | 11/1995 | Walthall et al. | |
| 5,470,152 A | 11/1995 | Rains | |
| 5,478,149 A | 12/1995 | Quigg | |
| 5,533,804 A * | 7/1996 | Larsson et al. | 366/274 |
| 5,672,481 A | 9/1997 | Minshall et al. | |
| 5,684,712 A * | 11/1997 | Goffe et al. | 700/285 |
| 5,733,776 A | 3/1998 | Barngrover et al. | |
| 5,750,440 A * | 5/1998 | Vanell et al. | 438/692 |
| 5,803,137 A * | 9/1998 | Shimotoyodome et al. | 141/67 |
| 5,899,567 A | 5/1999 | Morris, Jr. | |
| 5,941,867 A | 8/1999 | Kao | |
| 6,083,587 A | 7/2000 | Smith et al. | |
| 6,245,555 B1 | 6/2001 | Curtis | |
| 6,332,706 B1 | 12/2001 | Hall | |
| 6,416,215 B1 | 7/2002 | Terentiev | |
| 6,494,613 B1 | 12/2002 | Terentiev | |
| 6,670,171 B1 | 12/2003 | Carll | |
| 6,709,862 B1 | 3/2004 | Curtis | |
| 6,758,593 B1 * | 7/2004 | Terentiev | 366/273 |
| 6,837,610 B1 * | 1/2005 | Cadogan et al. | 366/144 |
| 6,837,613 B1 * | 1/2005 | Terentiev | 366/273 |
| 6,899,454 B1 * | 5/2005 | Terentiev | 366/273 |
| 2001/0039369 A1 | 11/2001 | Terentiev | |
| 2002/0082173 A1 | 6/2002 | Terentiev | |
| 2002/0105856 A1 | 8/2002 | Terentiev | |
| 2002/0131654 A1 | 9/2002 | Smith et al. | |
| 2002/0145940 A1 | 10/2002 | Terentiev | |
| 2003/0077466 A1 | 4/2003 | Smith et al. | |
| 2004/0047232 A1 | 3/2004 | Terentiev | |
| 2004/0062140 A1 | 4/2004 | Cadogan et al. | |
| 2004/0190372 A1 * | 9/2004 | Goodwin et al. | 366/273 |
| 2004/0218468 A1 | 11/2004 | Terentiev | |
| 2004/0245144 A1 * | 12/2004 | Hurst | 206/527 |
| 2005/0002274 A1 * | 1/2005 | Terentiev | 366/273 |
| 2005/0117449 A1 * | 6/2005 | Terentiev | 366/273 |
| 2005/0201201 A1 * | 9/2005 | Terentiev | 366/273 |

FOREIGN PATENT DOCUMENTS

| | | |
|---|---|---|
| WO | WO 03/028869 A2 | 4/2003 |

OTHER PUBLICATIONS

LevTech, Inc., *Business Plan*, pp. 1, 8, 9, 11, 12, 13, and 25, Sep. 5, 2000.

Mechanical drawing of Bottom Drain Barrel sold by HyClone Laboratories, Inc., at least as early as Jan. 2002.

* cited by examiner

CONTAINER SYSTEMS FOR MIXING FLUIDS WITH A MAGNETIC STIR BAR

CROSS-REFERENCE TO RELATED APPLICATIONS

This application claims priority to U.S. Provisional Patent Application Ser. No. 60/458,677, filed on Mar. 28, 2003 which is incorporated herein by specific reference.

BACKGROUND OF THE INVENTION

1. The Field of the Invention

The present invention relates to container systems for mixing and storing fluids.

2. The Relevant Technology

The mixing and/or suspension of solutions is ubiquitous in many technologies. For example, biotech companies use extensive amounts of culture media, buffers, and reagents. Such materials originally come in powdered form and must be hydrated with purified water prior to use. The hydration process typically comprises combining a precise amount of powdered material and purified water in a closed stainless steel tank. A special mixer is then used to mix the components into the desired solution. Liquid supplements can be added before or after the initial mixing. Once the solution is prepared, the solution is filtered and may be directly used or dispensed and sealed into sterile containers for shipment or storage.

To be safe and effective for their intended use, solutions of culture media, buffers, and reagents must be pure and sterile. Accordingly, between the production of different batches of solutions, the mixing tank, mixer, and all other reusable components that contact the solution must be carefully cleaned to avoid any cross contamination. The cleaning of the structural components is labor intensive, time consuming, and costly. For example, depending on the structural component and the solution being produced, cleaning can require the use of chemical cleaners such as sodium hydroxide and may require steam sterilization as well.

In another example, the production of vaccines or the culturing of cells typically requires that such solutions be continually mixed so that the components thereof remain uniformly dispersed as a homogeneous solution. Again, however, although steel tanks and mixers can be used to maintain such suspension and dispersion, conventional systems require that the tanks and mixers be carefully cleaned between batches to avoid any cross contamination.

Accordingly, what is needed in the art are container systems which minimize the time, cost, and labor associated with cleaning and sterilizing conventional systems while enabling mixing and/or suspension of solutions.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

The present invention relates to container systems that enable a user to hydrate powders, suspended components of a liquid, and/or otherwise mix solutions without the need for extensive cleaning of the systems between batches. The container systems of the present invention can be used in association with culture media, buffers, reagents and other solutions commonly used in the biotech industry and can also used in association with a vast array of other solutions outside of the biotech industry.

Figure 1:
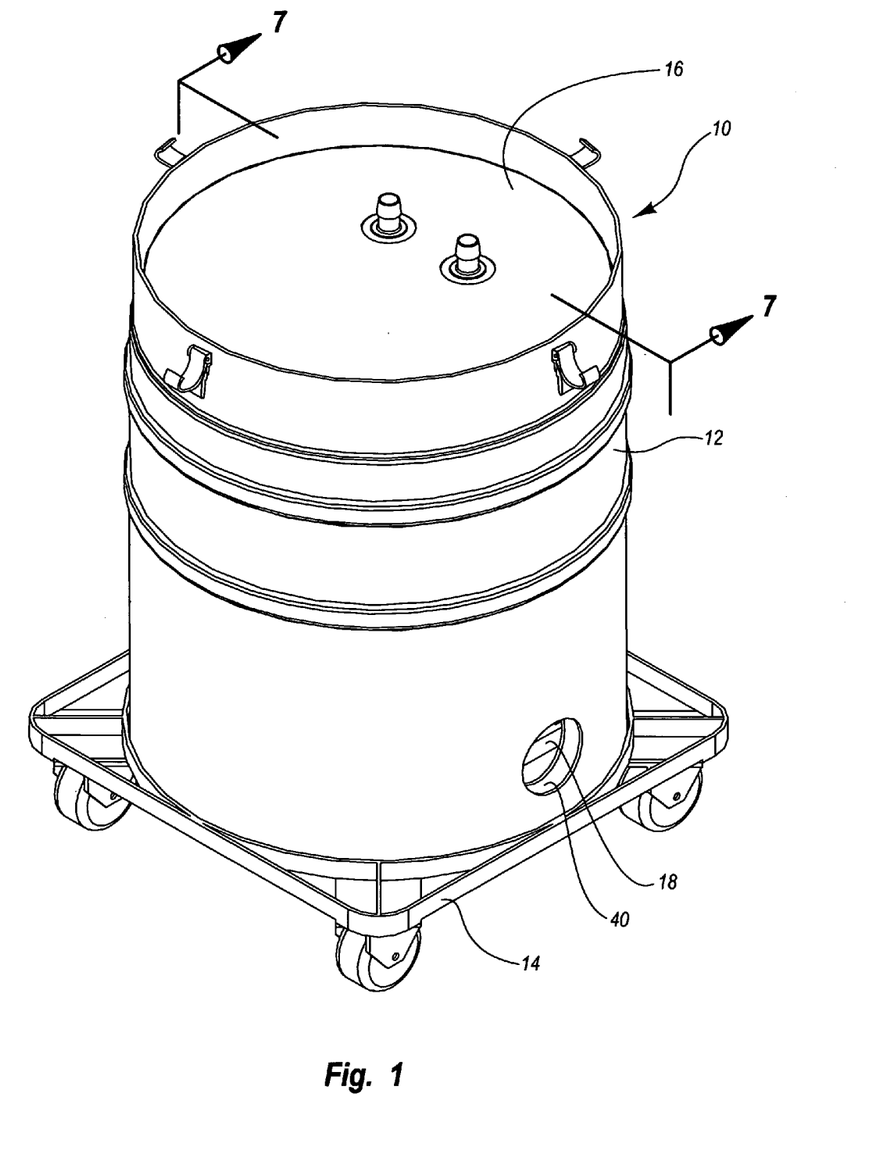
FIG. 1 is a perspective view of a container system.
Figure 2:
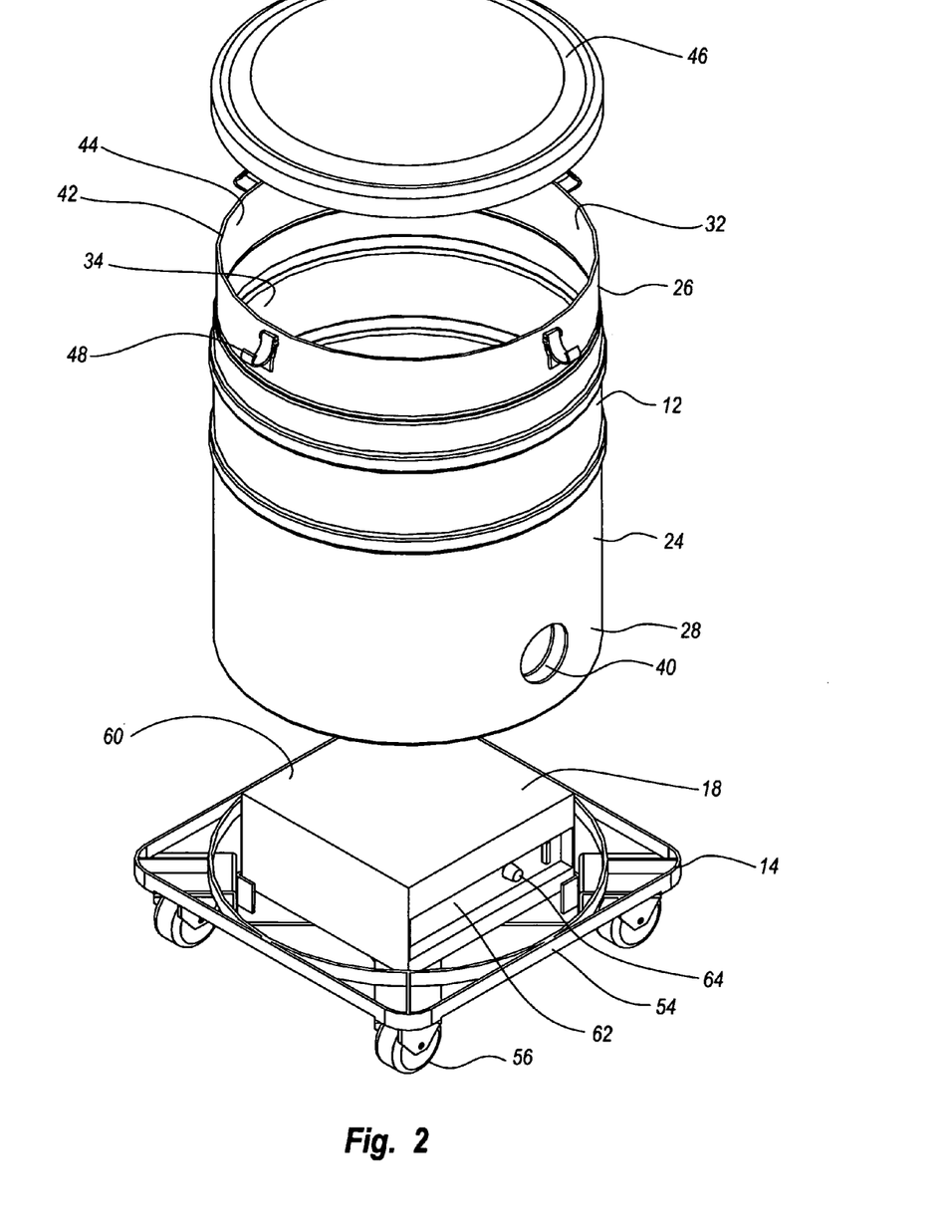
FIG. 2 is a partially exploded perspective view of a portion of the container system shown in FIG. 1.

Depicted in FIG. 1 is one embodiment of a container system 10 incorporating features of the present invention. In general, container system 10 includes a substantially rigid container 12 seated on a dolly 14. Disposed within container 12 is a mixing bag assembly 16. Disposed between mixing bag assembly 16 and dolly 14 is a magnetic mixer 18 (FIG. 2). As will be discussed below in greater detail, magnetic mixer 18 is used to mix a solution disposed within mixing bag assembly 16.

Figure 3:
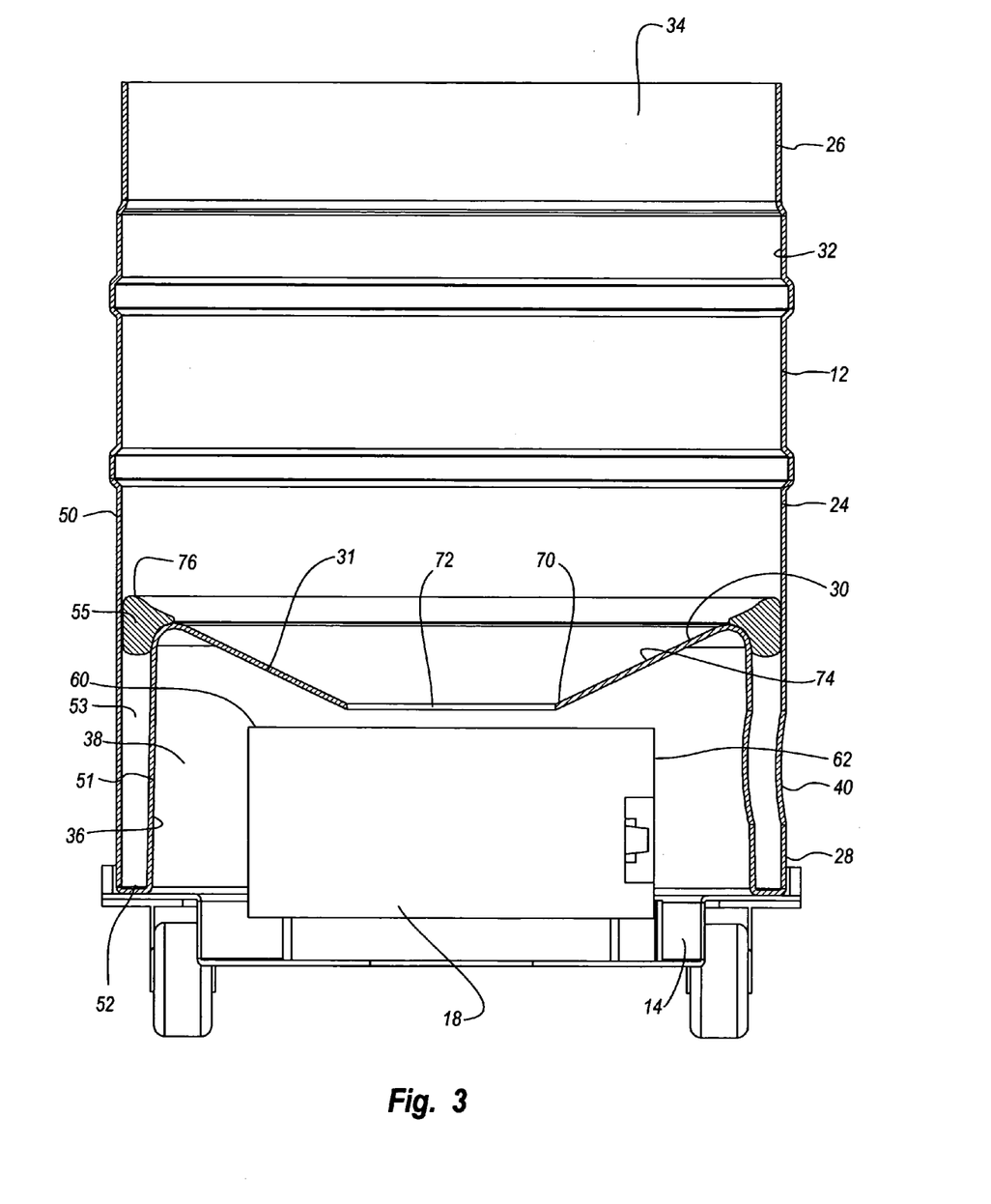
FIG. 3 is a cross sectional side view of the system shown in FIG. 2 without the lid thereof.

As depicted in FIG. 2, container 12 comprises a substantially cylindrical side wall 24 that extends from an upper end 26 to an opposing lower end 28. As depicted in FIG. 3, container 12 includes a floor 30 formed inside of container 12 at a position between upper end 26 and lower end 28. Floor 30 has a substantially frustaconical configuration. More specifically, floor 30 has top surface 74 that extends between an inner edge 70 and an opposing outer edge 76. Inner edge 70 bounds a central opening 72 extending through floor 30. Outer edge 76 is integrally formed with or is otherwise connected to side wall 24.

For example, in the embodiment depicted side wall 24 comprises an outer wall 50 that extends between opposing ends 26 and 28 and an inner wall 51 that extends from a central portion 31 of floor 30 to lower end 28. An annular transition 52 connects outer wall 50 and inner wall 51 at lower end 28. Above transition 52, outer wall 50 and inner wall 51 are spaced apart so as to form an annular gap 53. An annular seal 55 is disposed within gap 53 so as to form a bridge between outer wall 50 and inner wall 51 at the location where inner wall 51 connects with central portion 31 of floor 30. Seal 55 combines with central portion 31 to form floor 30. In part, seal 55 functions to prevent mixing bag assembly 16 from sliding into gap 53 which could cause failure of mixing bag assembly 16.

In this embodiment, container 12 is molded so that outer wall 50, inner wall 51, transition 52, and central portion 31 of floor 30 are all integrally formed as a single mold item. In alternative embodiments, inner wall 51 and seal 55 can be eliminated. This can be accomplished by integrally molding floor 30 directly to outer wall 50 or by having a discrete floor 30 that is connected to outer wall 50.

Top surface 74 of floor 30 slopes radially outward and upward from inner edge 70 to outer edge 76. Floor 30 thus functions in part as a funnel to direct all material toward central opening 72. In alternative embodiments, floor 30 can be flat, cupped, irregular, or other desired configurations.

Side wall 24 of container 12 has an interior surface 32 disposed above floor 30. Interior surface 32 and floor 30 bound a first chamber 34 formed in upper end 26 of container 12. First chamber 34 can be sized to have any desired volume. For example, first chamber 34 can be sized to hold 50 liters, 100 liters, 200 liters, or other desired amounts. Depicted in FIG. 2, upper end 26 of container 12 terminates at an upper edge 42 that bounds an opening 44 to first chamber 34. An optional annular lid 46 can be removably disposed over upper edge 42 so as to selectively close opening 44. Clamps 48 are used to selectively secure lid 46 to container 12.

Returning to FIG. 3, side wall 24 also has an interior surface 36 formed below floor 30. Interior surface 36 and floor 30 bound a second chamber 38 disposed at lower end 28 of container 12. An access port 40 extends through side wall 24 at lower end 28 of container 12 so as to provide side access to second chamber 38. In alternative embodiments, the portion of side wall 24 extending below floor 30 can be replaced with one or more spaced apart legs or other supports that elevate floor 30 off of the ground, dolly 14, or other surface on which container 12 rests.

In the embodiment depicted, container 12 comprises a barrel molded from a polymeric material. In alternative embodiments, container 12 can be comprised of metal, fiberglass, composites, or any other desired material. Furthermore, although container 12 is shown as having a substantially cylindrical configuration, container 12 can be substantially boxed shaped or have a transverse configuration that is polygonal, elliptical, irregular, or any other desired configuration.

As depicted in FIG. 2, dolly 14 comprises a frame 54 having a plurality of wheels 56 mounted thereon. Dolly 14 enables easy movement of container 12. In alternative embodiments where it is not necessary or desired to move container 12, wheels 56 and/or frame 54 can be eliminated. In this regard, container 12 can sit on a ground surface or any other desired structure.

Magnetic mixer 18 is mounted on dolly 14. Magnetic mixer 18 is a standard off-the-shelf item that uses a magnetic force to rotate a magnetic stir rod which will be discussed below in greater detail. One example of magnetic mixer 18 comprises the MAXISTIRRER Model #S25530 240V available from Barnstead/Thermolyne out of Dubuque, Iowa. Magnetic mixer 18 has a top surface 60 and a front face 62. Switches 64 are positioned on front face 62 and are used for turning magnetic mixer 18 on and off and for adjusting the speed at which magnetic mixer 18 rotates a magnetic stir bar.

Depicted in FIG. 3, lower end 28 of container 12 is received on dolly 14 such that magnetic mixer 18 is received with second chamber 38 directly below central opening 72 of floor 30. Container 12 is oriented such that access port 40 of container 12 is aligned with front face 62 of magnetic mixer 18. As a result, a user can reach through access port 40 for selectively activating and controlling magnetic mixer 18.

Figure 4:
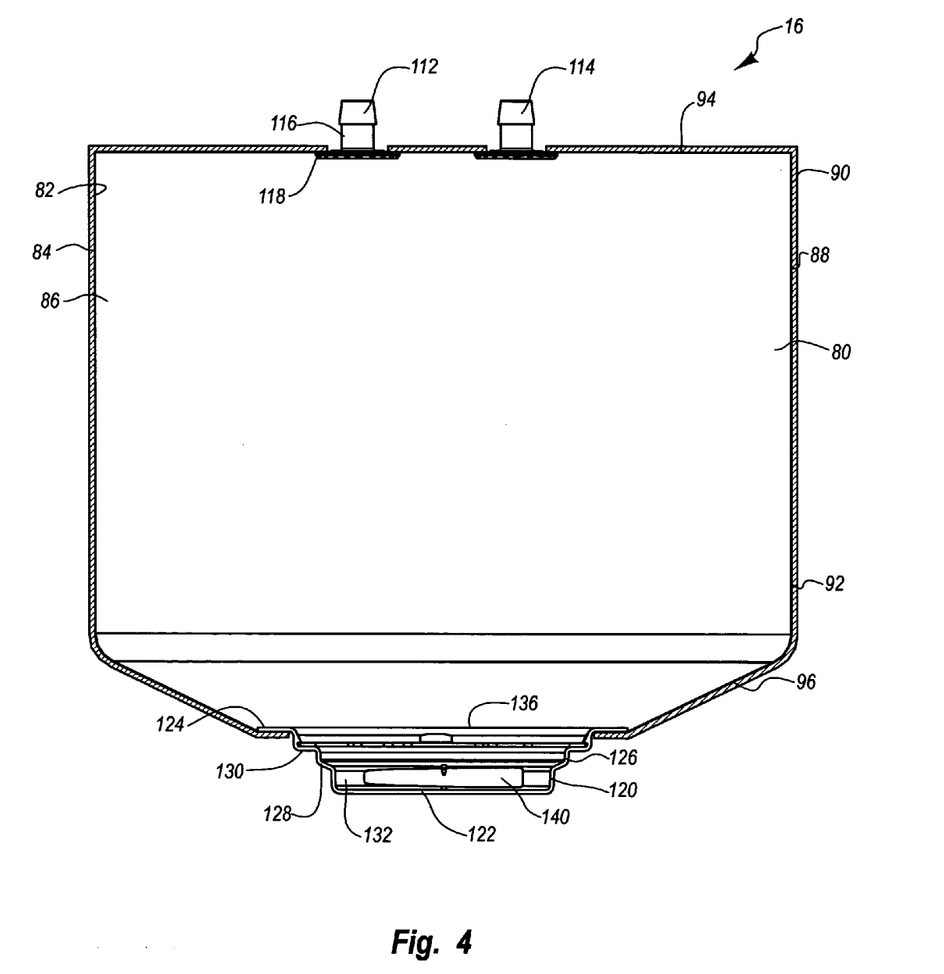
FIG. 4 is a cross sectional side view of the mixing bag assembly shown in FIG. 1.

Depicted in FIG. 4 is a cross sectional side view of mixing bag assembly 16. Mixing bag assembly 16 comprises a flexible and collapsible bag-like body 80 having an interior surface 82 and an exterior surface 84. Interior surface 82 bounds a compartment 86. More specifically, body 80 comprises a side wall 88 that, when body 80 is unfolded, has a substantially circular or polygonal transverse cross section that extends between a first end 90 and an opposing second end 92. First end 90 terminates at a top end wall 94 while second end 92 terminates at a bottom end wall 96.

Body 80 is comprised of a flexible, water impermeable material such as polyethylene or other polymeric sheets having a thickness in a range between about 0.1 mm to about 5 mm with about 0.2 mm to about 2 mm being more common. Other thicknesses can also be used. The material can be comprised of a single ply material or can comprise two or more layers which are either sealed together or separated to form a double wall container. Where the layers are sealed together, the material can comprise a laminated or extruded material. The laminated material comprises two or more separately formed layers that are subsequently secured together by an adhesive.

The extruded material comprises a single integral sheet which comprises two or more layer of different material separated by a contact layer that are all simultaneously co-extruded. Once example of an extruded material that can be used in the present invention is the HyQ CX5-14 cast film available from HyClone Laboratories, Inc. The HyQ CX5-14 cast film comprises a polyester elastomer outer layer, an ultra-low density polyethylene contact layer, and an EVOH barrier layer disposed therebetween. Another example of film that can be used is the Attane film which is also available from HyClone Laboratories, Inc. The Attane film is produced from three independent webs of blown film. The two inner webs are a 4 mil monolayer polyethylene film, while the outer barrier web is a 5.5 mil thick 6-layer coextrusion film.

In one embodiment, the material is approved for direct contact with living cells and is capable of maintaining a solution sterile. In such an embodiment, the material can also be sterilizable such as by ionizing radiation. Other examples of materials that can be used are disclosed in U.S. Pat. No. 6,083,587 which issued on Jul. 4, 2000 and U.S. patent application Ser. No. 10/044,636, filed Oct. 19, 2001 which are hereby incorporated by specific reference.

In one embodiment, body 80 comprises a two-dimensional pillow style bag wherein two sheets of material are placed in overlapping relation and the two sheets are bounded together at their peripheries to form internal compartment 86. Alternatively, a single sheet of material can be folded over and seamed around the periphery to form internal compartment 86. In the embodiment depicted, however, body 80 comprises a three-dimensional bag which not only has an annular side wall 88 but also a two dimensional top end wall 94 and a two dimensional bottom end wall 96.

Three dimensional body 80 comprises a plurality, i.e., typically three or more, discrete panels. Depicted in FIG. 5A, body 80 is comprised of four panels, i.e., top panel 98, front panel 99, back panel 100, and bottom panel 101. Each panel 98–101 has a substantially square or rectangular central portion 104. Top panel 98 and bottom panel 101 include a first end portion 106 and an opposing second end portion 108 projecting from opposing ends of central portion 104. Each of end portions 106 and 108 has a substantially trapezoidal configuration with opposing tapered edges 110. Front panel 99 and back panel 100 each include a triangular first end portion 107 and an opposing triangular second end portion 109 projecting from opposing ends of central portion 104.

Figure 5A:
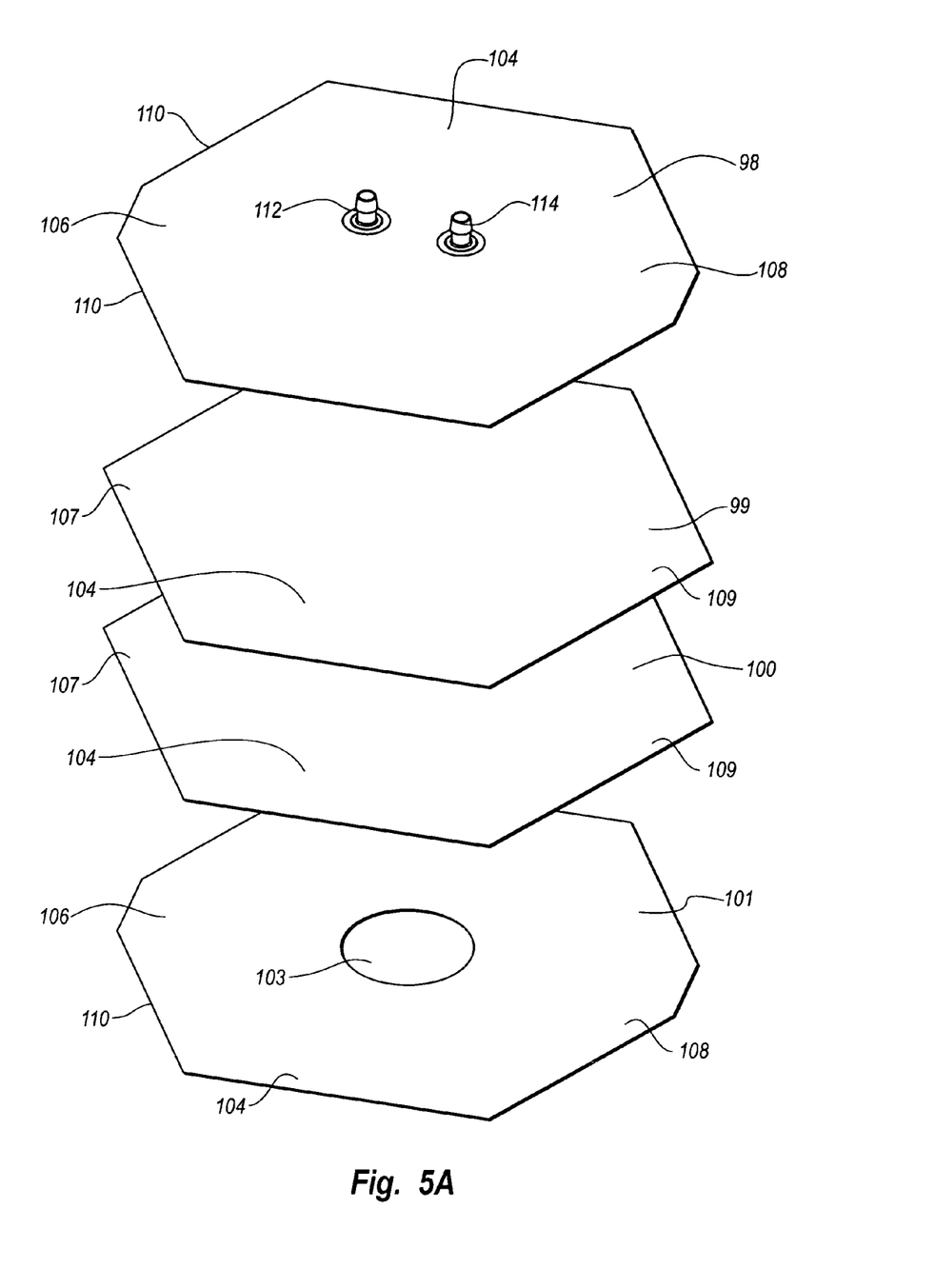
FIG. 5A is a perspective view of the panels of the mixing bag assembly shown in FIG. 4.
Figure 5B:
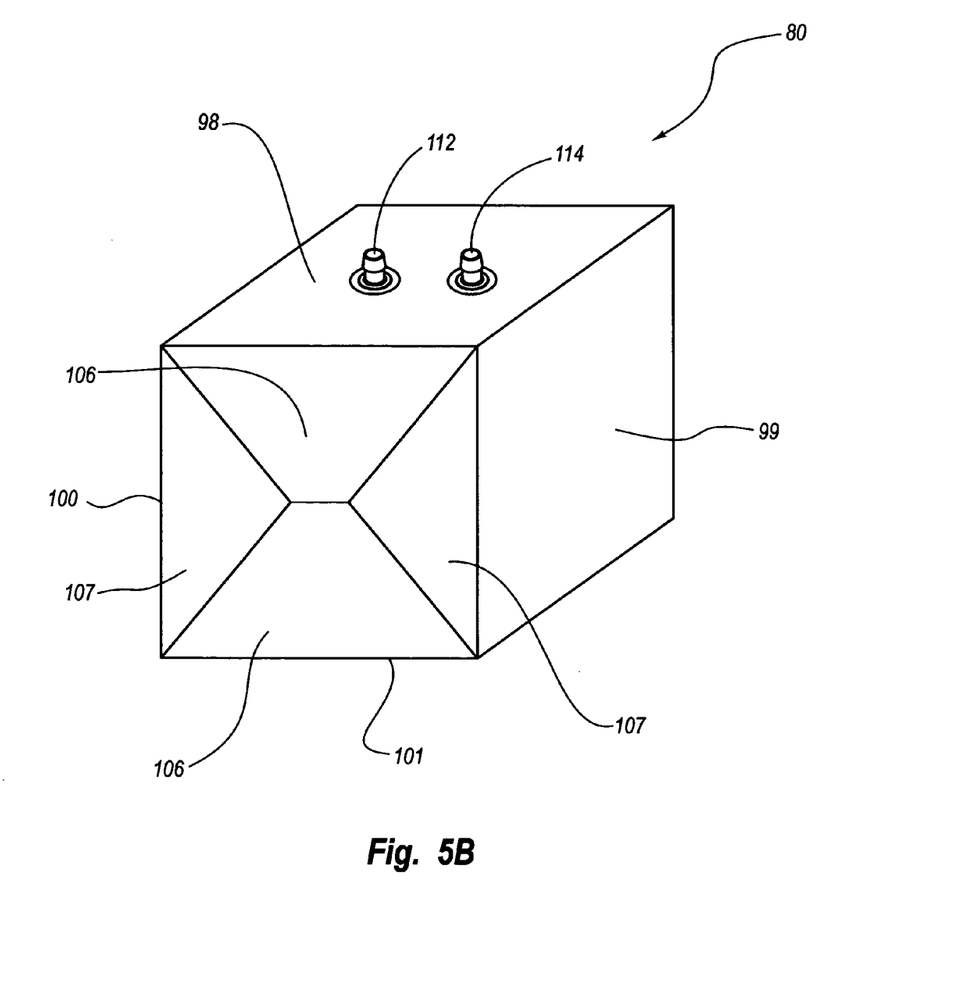
FIG. 5B is a perspective view of the panels shown in FIG. 5A seamed together.

As depicted in FIG. 5B, corresponding perimeter edges of each panel 98–101 are seamed together so as to form a substantially box shaped body 80. Panels 98–101 are seamed together using methods known in the art such as heat energies, RF energies, sonics, other sealing energies, adhesives, or other conventional processes. It is appreciated that by altering the size and configuration of some or all of panels 98–101, body 80 can be formed having a variety of different sizes and configurations. It is also appreciated that any number of panels can be used to adjust the size and configuration of body 80.

In still other embodiments, it is appreciated that body 80 can be formed by initially extruding or otherwise forming a polymeric sheet in the form of a continuous tube. In one embodiment, the tube can simply be cut to length and each end seamed closed to form a two-dimensional pillow style bag. In an alternative embodiment, each end can be folded like the end of paper bag and then seamed closed so as to form a three dimension body. In still another embodiment, a length of tube can be laid flat so as to form two opposing folded edges. The two folded edges are then inverted inward so as to form a pleat on each side. The opposing end of the tube are then seamed closed. Finally, an angled seam is formed across each corner so as to form a three dimensional bag when inflated.

It is appreciated that the above techniques can be mixed and matched with one or more polymeric sheets and that there are still a variety of other ways in which body 80 can be formed having a two or three dimensional configuration. Further disclosure with regard to one method of manufacturing three-dimensional bags is disclosed in U.S. patent application Ser. No. 09/813,351, filed on Mar. 19, 2001 of which the drawings and Detailed Description are hereby incorporated by specific reference.

It is appreciated that body 80 can be manufactured to have virtually any desired size, shape, and configuration. For example, body 80 can be formed having compartment 86 sized to hold 50 liters, 100 liters, 200 liters, or other desired amounts. Although body 80 is depicted in FIG. 5B having a substantially box shaped configuration, body 80, as depicted in FIG. 4, conforms to the configuration of first chamber 34 as it is filled with solution. In one embodiment, however, body 80 can be specifically configured to be complementary or substantially complementary to first chamber 34.

In any embodiment, however, it is desirable that when body 80 is received within first chamber 34, body 80 is uniformly supported by floor 30 and side wall 24 of container 12. Having at least generally uniform support of body 80 by container 12 helps to preclude failure of body 80 by hydraulic forces applied to body 80 when filled with a solution.

As depicted in FIG. 4, mounted on top end wall 94 of body 80 are a pair of spaced apart ports 112 and 114. Each port 112 and 114 comprises a barbed tubular stem 116 having a flange 118 outwardly projecting from an end thereof. During assembly, a pair of spaced apart holes are made through top panel 98 (FIG. 5A and B) prior to complete seaming together of panels 98–101. The stem 116 of each port 112 and 114 is then passed through a corresponding hole until flange 118 rests against panel 98. Conventional welding or other sealing techniques are then used to seal each flange 118 to panel 98. During use, stem 116 is selectively coupled with a tube or container for delivering material into and/or out of compartment 86. It is appreciated that any number of ports can be formed on body 80 and that a variety of different types and sizes of ports can be used depending on the type of material to be dispensed into compartment 86 and how the material is to be dispensed therefrom.

Figure 6:
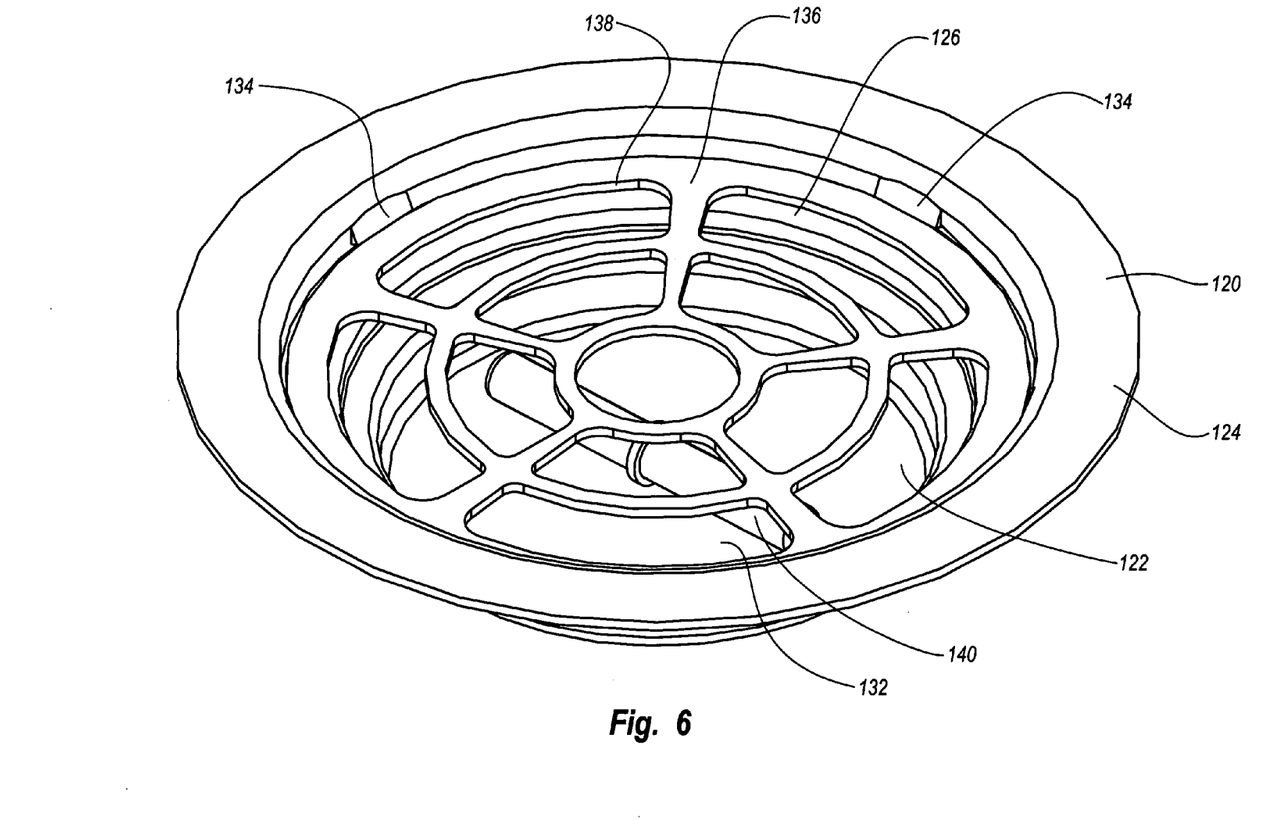
FIG. 6 is a perspective view the mixing dish, retention plate, and stir bar shown in FIG. 4.

Mounted on bottom end wall 96 of body 80 is a mixing dish 120. As depicted in FIGS. 4 and 6, mixing dish 120 comprises a substantially flat floor 122 and an annular outer perimeter flange 124. A substantially frustaconical side wall 126 encircles floor 122 and outwardly and upwardly extends to perimeter flange 124. Side wall 126 includes an annular first shoulder 128 and an annular second shoulder 130. Side wall 126 and floor 124 bound a cavity 132. Inwardly projecting from side wall 126 directly above second shoulder 130 are a plurality of spaced apart catches 134.

As with ports 112 and 114, during assembly a hole 103 is formed in bottom panel 101 (FIG. 5A). Mixing dish 120 is seated within the hole 103 so that outer perimeter flange 124 rests against bottom panel 101. Again, conventional welding or other sealing techniques are then used to seal perimeter flange 124 to bottom panel 101.

An annular retention plate 136 bounds a plurality of openings 138 extending therethrough. Retention plate 136 is removably attached to mixing dish 120 by pushing retention plate 136 onto second shoulder 130 so that retention plate 136 is caught between second shoulder 130 and catches 134. Due to openings 138 formed on retention plate 136, cavity 132 is in fluid communication with compartment 86 of body 80.

In one embodiment, mixing dish 120 is integrally molded from a polymeric material, such as high density polyethylene, and has a thickness in a range between about 1 mm to about 5 mm. Mixing dish 120 is more rigid than body 80 and in one embodiment is substantially rigid so as to prevent unwanted bending or flexing during use.

Disposed within cavity 132 of mixing dish 120 and resting on floor 122 thereof is a conventional off-the-shelf magnetic stir bar 140. Stir bar 140 is typically sold as a unit with magnetic mixer 18 and is configured to selectively rotate within cavity 132 under the control of magnetic mixer 18. That is, magnetic mixer 18 controls the speed and variability at which stir bar 140 rotates.

Figure 7:
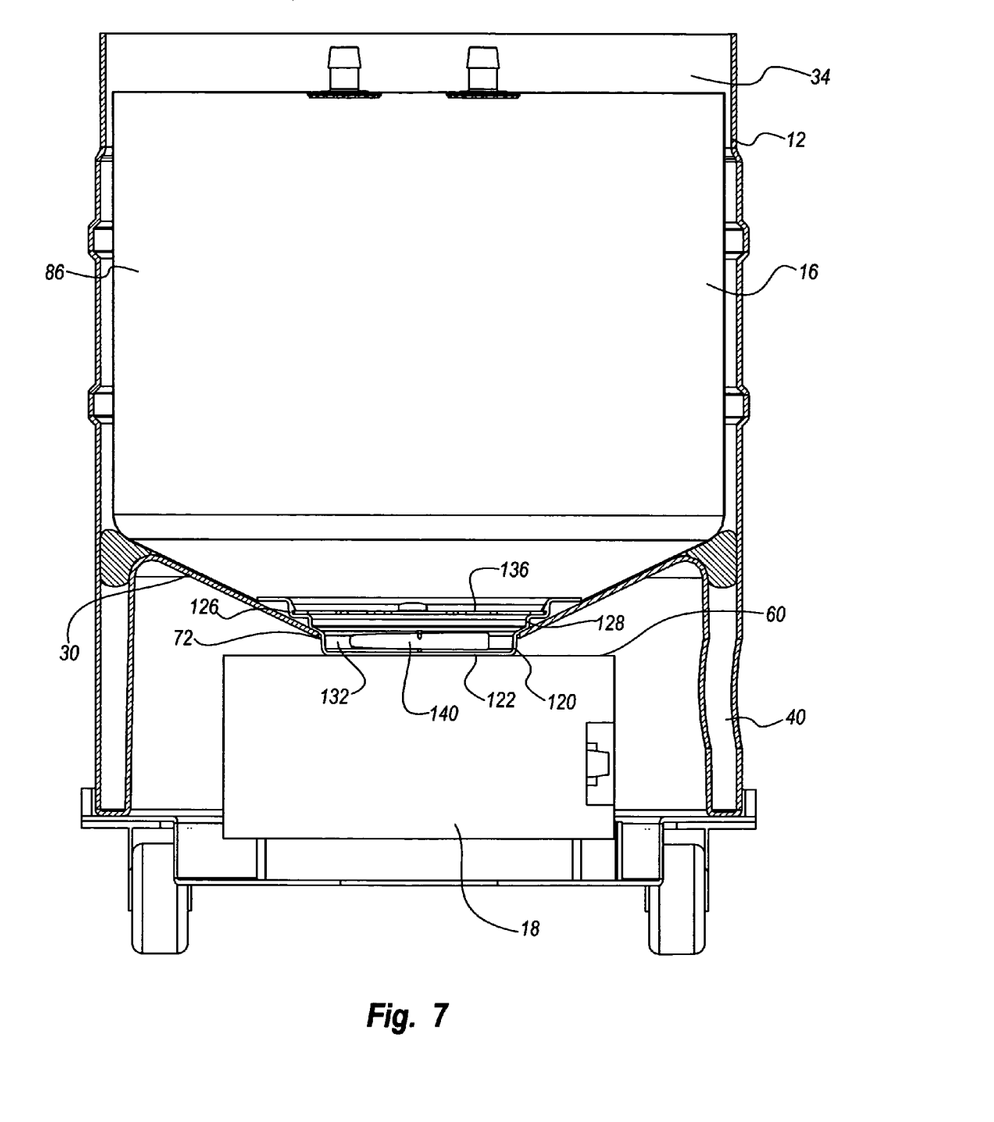
FIG. 7 is a cross sectional side view of the container system shown in FIG. 1 taken along section line 7—7.

Once ports 112, 114 and mixing dish 120 are sealed to their corresponding panel and stir bar 120 is captured within mixing dish 120 by retention plate 136, panels 98–101 are seamed together so as to complete the formation of bag 80 and bag assembly 16. During use, as depicted in FIG. 7, mixing bag assembly 16 is disposed within first chamber 34 of container 12 so that floor 122 of mixing dish 120 is received within central opening 72 extending through floor 30 of container 12. Annular first shoulder 128 of mixing dish 120 supports mixing dish 120 on floor 30 of container 12. In this configuration, floor 122 of mixing dish 120 is disposed above or directly on top surface 60 of magnetic mixer 18.

Tubes or containers are then coupled to at least one of ports 112 and 114 for delivering a solution or components for a solution into compartment 86 of mixing bag assembly 16. At least one of the components can be a substantially dry material such as a powder, granule, or other form of dry material. Alternatively, all of the components can be liquid. Once the solution or components are within compartment 86 of mixing bag assembly 16, magnetic mixer 18 is activated so that magnetic stir bar 140 is rotated within mixing dish 120. In turn, stir bar 140 mixes the solution or components within compartment 86. Depending on the selected speed of magnetic mixer 18, stir bar 140 can form a vortex within the solution.

Side wall 126 of mixing dish 120 and retention plate 136 in part function to retain stir bar 140 within cavity 132 during transport of mixing bag assembly 16 and the initial activation of magnetic mixer 18. That is, stir bar 140 will often jump around as magnetic mixer 18 is initially activated. Side wall 126 and retention plate 136 help to maintain stir bar 140 within cavity 132 until it obtains smooth rotation. The flat and substantially rigid floor 122 of mixing dish 120 assists in expediting the rate as which stir bar 140 moves into a smooth rotation.

Depending on the type of solution being mixed, the solution can be selectively drawn out of mixing bag assembly 16 either while the mixing is occurring and/or after completion of the mixing and magnetic mixer 18 is turned off. Once the solution is removed, mixing bag assembly can simply be disposed of such as by being discarded or recycled. A new mixing bag assembly 16 is then inserted within container 12 and the process can be repeated for a new batch of solution. As a result, no tank or mixer cleaning is required between different batches and there is no risk of cross contamination. Of course where cross contamination is not a concern, mixing bag assembly 16 can be used repeatedly for different batches until the assembly is worn or a non-compatible batch is to be made.

In alternative embodiments, it is appreciated that mixing dish 120 can come in a variety of alternative configurations. For example, retention plate 136 is not required but can produce some functional benefits. Furthermore, mixing dish 120 need not be bowl shaped but can comprise a substantially flat plate. In this embodiment, floor 30 of container 12 can be sufficiently tapered to help ensure that stir bar 140 remains on the mixing dish. In yet other embodiments of the present invention, it is noted that central opening 72 can be eliminated on floor 30 of container 12, i.e., a flat section of floor 30 can extend across prior opening 72. In this embodiment, mixing dish 120 sits directly on the flat section of floor 30 above magnetic mixer 18.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A mixing bag assembly comprising:
   a body bounding a compartment, the body being comprised of a flexible sheet;
   a mixing dish secured to the body, the mixing dish having a floor and an annular side wall upstanding from the floor, the floor being in communication with the compartment of the body, and the side wall terminating at a perimeter edge, the perimeter edge being secured to the body, the side wall and the floor of the mixing dish bounding a cavity;
   a magnetic stir bar disposed within the cavity; and
   a retention cover mounted to the mixing dish so as to further bound the stir bar within the cavity, the retention cover having at least one opening extending therethrough.

2. A mixing bag assembly as recited in claim 1, wherein the body comprises a two-dimensional pillow style bag or a three dimensional bag.

3. A mixing bag assembly as recited in claim 1, wherein the body comprises at least three polymeric panels seamed together.

4. A mixing bag assembly as recited in claim 1, wherein the retention cover has a plurality of openings extending therethrough.

5. A mixing bag assembly as recited in claim 1, wherein the retention cover is removably mounted to the side wall of the mixing dish.

6. A mixing bag assembly as recited in claim 1, wherein the mixing dish is more rigid than the body.

7. A mixing bag assembly as recited in claim 1, wherein the mixing dish is substantially rigid.

8. A mixing bag assembly as recited in claim 1, wherein the mixing dish comprises a substantially flat plate secured to the body.

9. A mixing bag assembly as recited in claim 1, further comprising at least one fluid port mounted on the body so as to communicate with the compartment of the body.

10. A mixing bag assembly as recited in claim 1, wherein the compartment of the body has a volume of at least 50 liters.

11. A mixing bag assembly as recited in claim 1, wherein the body has a hole extending therethrough, the mixing dish being at least partially disposed within the hole and secured to the body.

12. A mixing bag assembly as recited in claim 1, wherein the mixing dish has an interior surface and an opposing exterior surface, at least a portion of the interior surface being in communication with the compartment of the body, at least a portion of the exterior surface not being in communication with the compartment of the body.

13. A mixing bag assembly as recited in claim 1, wherein the mixing dish is sealed to the body.

14. A container system comprising:
    a substantially rigid container having a floor, an upper side wall upstanding therefrom, and a lower side wall downwardly extending from the floor, the upper side wall and floor bounding a first chamber, and the lower side wall bounding a second chamber;
    a magnetic mixer disposed below the floor of the container, the magnetic mixer being at least partially disposed within the second chamber; and
    a mixing bag assembly at least partially disposed within the first chamber of the container, the mixing bag assembly comprising:
      a collapsible body bounding a compartment, the body having a first end and an opposing second end, at least a portion of the second end of the body resting on or adjacent to the floor of the container,
      a mixing dish being more rigid than the collapsible body, the mixing dish being secured at the second end of the collapsible body; and
      a magnetic stir bar disposed on the mixing dish.

15. A container system as recited in claim 14, wherein the floor is integrally formed with the upper side wall of the container.

16. A container system as recited in claim 14, wherein at least a portion of the mixing dish is resting on the floor of the container.

17. A container system as recited in claim 14, wherein the floor has an opening extending therethrough, at least a portion of the mixing dish extending through the opening on the floor.

18. A container system as recited in claim 14, wherein the mixing dish is disposed directly on or adjacent to the magnetic mixer.

19. A container system as recited in claim 14, wherein the lower side wall of the container is integrally formed with the upper side wall and the floor.

20. A container system as recited in claim 14, further comprising an access port formed through the lower side wall so as to enable access to the second chamber.

21. A container system as recited in claim 14, further comprising a dolly having a frame with wheels mounted thereon, the container and magnetic mixer being supported on the frame of the dolly.

22. A container system as recited in claim 14, wherein the upper side wall of the container terminates an edge bounding a top opening, a lid being removably mounted on the upper side wall so as to cover the top opening.

23. A container system as recited in claim 14, wherein the body of the mixing bag comprises a two-dimensional pillow style bag or a three dimensional bag.

24. A container system as recited in claim 14, wherein the body of the mixing bag is comprised of a laminated or extruded polymer sheet comprised to two or more layers of different material.

25. A container system as recited in claim 14, wherein the mixing dish comprises an annular side wall extending between a floor and a perimeter edge, the perimeter edge being secured to the body.

26. A container system as recited in claim 25, further comprising:
the side wall and the floor of the mixing dish bound a cavity, the magnetic stir bar being disposed within the cavity; and
a retention cover mounted to the mixing dish so as to further bound the stir bar within the cavity, the retention cover having at least one opening extending therethrough.

27. A container system as recited in claim 14, wherein the body of the mixing bag has a hole extending therethrough, the mixing dish being at least partially disposed within the hole and secured to the body.

28. A container system as recited in claim 14, wherein the mixing dish has an interior surface and an opposing exterior surface, at least a portion of the interior surface being in communication with the compartment of the body, at least a portion of the exterior surface not being in communication with the compartment of the body.

29. A method comprising:
inserting a disposable mixing bag assembly within a substantially rigid container, the container having a floor with an opening extending therethrough, a magnetic stir bar being disposed within a compartment of the mixing bag assembly so that the stir bar is aligned with the opening on the floor of the container;
delivering a solution or at least two separate components into the compartment of the mixing bag assembly, at least one of the at least two separate components being a liquid; and
activating a magnetic mixer disposed below the opening on the floor of the container so as to cause rotation of the magnetic stir bar within the mixing bag assembly, the magnetic stir bar stirring the solution or the at least two separate components, wherein the mixing bag assembly comprises:
a body bounding the compartment, the body being comprised of at least one flexible sheet;
a mixing dish secured to the body, the mixing dish having a floor and an annular side wall upstanding therefrom, the side wall and the floor of the mixing dish bounding a cavity, the magnetic stir bar being disposed within the cavity, the act of inserting comprising at least partially positioning the mixing dish within the opening on the floor of the container; and
a retention cover mounted to the mixing dish so as to further bound the stir bar within the cavity, the retention cover having at least one opening extending therethrough.

30. A method as recited in claim 29, further comprising dispensing from the mixing bag assembly the solution or the at least two components that are stirred within mixing bag assembly.

31. A mixing bag assembly comprising:
a body bounding a compartment, the body being comprised of at least one flexible sheet;
a mixing dish assembly at least partially disposed on the body and at least partially bounding a cavity, a plurality of openings being formed on the mixing dish assembly, each opening providing fluid communication between the cavity of the mixing dish assembly and the compartment of the body; and
a magnetic stir bar disposed within the cavity of the mixing dish assembly.

32. A mixing bag assembly as recited in claim 31, wherein each opening on the mixing dish is sized so as to prevent the magnetic stir bar from freely passing from the cavity to the compartment.

33. A mixing bag assembly as recited in claim 31, wherein the mixing dish assembly comprises:
a mixing dish comprising a floor and a side wall upstanding therefrom; and
a retention plate mounted to the side wall.

34. A mixing bag assembly as recited in claim 31, wherein at least a portion of the mixing dish assembly is secured to the body.

35. A container system comprising:
a substantially rigid container having a floor and an upper side wall upstanding therefrom, the upper side wall and floor bounding a first chamber;
a magnetic mixer disposed below the floor of the container; and
a mixing bag assembly at least partially disposed within the first chamber of the container, the mixing bag assembly comprising:
a collapsible body bounding a compartment, the body having a first end and an opposing second end, at least a portion of the second end of the body resting on or adjacent to the floor of the container,
a mixing dish being more rigid than the collapsible body, the mixing dish comprising an annular side wall extending between a floor and a perimeter edge, the perimeter edge being secured to the second end of the body, the side wall and the floor of the mixing dish bounding a cavity; and
a magnetic stir bar disposed within the cavity; and
a retention cover mounted to the mixing dish so as to further bound the stir bar within the cavity, the retention cover having at least one opening extending therethrough.

36. A container system as recited in claim 35, wherein the retention cover has a plurality of openings extending therethrough.

37. A container system as recited in claim 36, wherein the retention cover is removably mounted to the side wall of the mixing dish.

38. A container system as recited in claim 36, further comprising at least one fluid port mounted on the first end of the body of the mixing bag so as to communicate with the compartment of the body.

* * * * *

UNITED STATES PATENT AND TRADEMARK OFFICE
CERTIFICATE OF CORRECTION

PATENT NO. : 7,153,021 B2  Page 1 of 1
APPLICATION NO. : 10/797159
DATED : December 26, 2006
INVENTOR(S) : Goodwin et al.

It is certified that error appears in the above-identified patent and that said Letters Patent is hereby corrected as shown below:

Column 4
Line 16, change "layer" to --layers--

Column 7
Line 1, change "as" to --at--

Column 9
Line 10, change "to" to --of--

Signed and Sealed this

Thirty-first Day of July, 2007

JON W. DUDAS
*Director of the United States Patent and Trademark Office*

UNITED STATES PATENT AND TRADEMARK OFFICE
CERTIFICATE OF CORRECTION

PATENT NO. : 7,153,021 B2  Page 1 of 1
APPLICATION NO. : 10/797159
DATED : December 26, 2006
INVENTOR(S) : Goodwin et al.

It is certified that error appears in the above-identified patent and that said Letters Patent is hereby corrected as shown below:

Column 2
Line 22, after "also" insert --be--

Column 4
Line 16, change "layer" to --layers--
Line 18, change "Once" to --One--

Column 5
Lines 16-17, change "end of the tube" to --ends of the tubes--

Column 6
Line 4, change "124" to --122--
Line 36, change "120" to --140--

Column 7
Line 1, change "as" to --at--

Column 9
Line 10, change "to" to --of--

This certificate supersedes the Certificate of Correction issued July 31, 2007.

Signed and Sealed this

Tenth Day of June, 2008

JON W. DUDAS
*Director of the United States Patent and Trademark Office*